US007375321B2

(12) United States Patent
Roukes et al.

(10) Patent No.: US 7,375,321 B2
(45) Date of Patent: May 20, 2008

(54) DYNAMICS BIONEMS SENSORS AND ARRAYS OF BIONEMS SENSOR IMMERSED IN FLUIDS

(75) Inventors: Michael L. Roukes, Pasadena, CA (US); Scott E. Fraser, La Canada, CA (US); Jerry E. Solomon, Glendale, CA (US); Jessica L. Arlett, Altadena, CA (US); Michael C. Cross, Claremont, CA (US)

(73) Assignee: California Institute of Technology, Pasadena, CA (US)

( * ) Notice: Subject to any disclaimer, the term of this patent is extended or adjusted under 35 U.S.C. 154(b) by 649 days.

(21) Appl. No.: 10/502,551

(22) PCT Filed: May 7, 2003

(86) PCT No.: PCT/US03/14284

§ 371 (c)(1),
(2), (4) Date: Feb. 15, 2005

(87) PCT Pub. No.: WO03/095616

PCT Pub. Date: Nov. 20, 2003

(65) Prior Publication Data

US 2007/0158553 A1 Jul. 12, 2007

Related U.S. Application Data

(63) Continuation-in-part of application No. 09/927,779, filed on Aug. 9, 2001.

(60) Provisional application No. 60/379,710, filed on May 7, 2002, provisional application No. 60/379,660, filed on May 7, 2002, provisional application No. 60/379,645, filed on May 7, 2002, provisional application No. 60/379,552, filed on May 7, 2002, provisional application No. 60/379,711, filed on May 7, 2002, provisional application No. 60/379,543, filed on May 7, 2002, provisional application No. 60/379,708, filed on May 7, 2002, provisional application No. 60/379,681, filed on May 7, 2002, provisional application No. 60/379,643, filed on May 7, 2002, provisional application No. 60/224,109, filed on Aug. 9, 2000.

(51) Int. Cl.
*G01N 13/16* (2006.01)

(52) U.S. Cl. ...................... 250/306; 250/307; 250/309; 702/19; 257/414

(58) Field of Classification Search ..................... None
See application file for complete search history.

(56) References Cited

U.S. PATENT DOCUMENTS 5,003,815 A 4/1991 Martin et al.
(Continued)

FOREIGN PATENT DOCUMENTS

| | | |
|---|---|---|
| WO | WO 98/50773 A2 | 11/1998 |
| WO | WO 00/58729 A2 | 10/2000 |
| WO | WO 01/33226 A1 | 5/2001 |

OTHER PUBLICATIONS

Baselt et al., "A High-Sensitiveity Micromachined Biosensor," Proceedings of the IEEE, Apr. 1997, 85(4):672-680.
(Continued)

*Primary Examiner*—Nikita Wells
(74) *Attorney, Agent, or Firm*—Foley & Lardner LLP

(57) ABSTRACT

A bioNEMS device comprises a piezoresistive cantilever having flexing legs of which attach the cantilever to a support and a biofunctionalized portion at the tip. A bias current applied to the legs is limited by a maximal acceptable temperature increase at the biofunctionalized tip. The length of the cantilever has a magnitude chosen to minimize background Johnson noise. A catalyzed receptor on the device binds to a ligand whose binding rate coefficient is enhanced. The catalyst lowers the receptor-ligand binding activation energy and is designed by forced evolution to preferentially bind with the ligand. A carrier signal is injected by a magnetic film disposed on the cantilever which is electromagnetically coupled to a source of the carrier signal. A plurality of NEMS fluidicly coupled transducers generate a plurality of output signals from which a collective output signal is derived, either by averaging or thresholding. The NEMS devices are disposed in microfluidic flow channels and fabricated in a membrane. A linking molecule is attached to the tip of the transducer and a fluffball attached to the linking molecule to increase damping.

34 Claims, 12 Drawing Sheets

U.S. PATENT DOCUMENTS

| | | | | |
|---|---|---|---|---|
| 5,282,924 | A | 2/1994 | Bayer et al. | |
| 5,481,527 | A | 1/1996 | Kasanuki et al. | |
| 5,559,330 | A | 9/1996 | Murashita | |
| 5,581,082 | A | 12/1996 | Hansma et al. | |
| 5,736,410 | A | 4/1998 | Zarling et al. | |
| 5,807,758 | A | 9/1998 | Lee et al. | |
| 6,006,594 | A | 12/1999 | Karrai et al. | |
| 6,289,717 | B1 | 9/2001 | Thundat et al. | |
| 6,559,474 | B1 | 5/2003 | Craighead et al. | |
| 6,722,200 | B2 | 8/2004 | Roukes et al. | |
| 2002/0166962 | A1* | 11/2002 | Roukes et al. | 250/306 |
| 2005/0161749 | A1 | 7/2005 | Roukes et al. | |
| 2006/0155478 | A1* | 7/2006 | Roukes et al. | 702/19 |

OTHER PUBLICATIONS

Baselt et al., "Biosensor based on force microscope technology," J. Vac. Sci. Technol., Mar./Apr. 1996, B 14(2):789-793; XP000613363.

Beck et al., "GaAs/AlGaAs self-sensing cantilevers for low temperature scanning probe microscopy," Appl. Phys. Lett., Aug. 24, 1988, 73(8):1149-1151, American Institue of Physics.

Binnig et al., "Atomic Force Microscope," Physical Review Letters, Mar. 3, 1986, 56(9):930-933.

Chui et al., "Independent detection of vertical and lateral forces with a sidewall-implanted dual-axis piezoresistive cantilever," Appl. Phys. Lett., Mar. 16, 1998, 72(11):1388-1390, American Institute of Physics.

Craighead, H.G., "Nanoelectromechanical Systems," Science, Nov. 24, 2000, 290:1532-1535; XP000941737.

Florin et al., "Adhesive Forces Between Individual Ligand-Receptor Paris," Science, Apr. 15, 1994, 264:415-417, American Association for the Advancement of Science.

Fritz et al., "Translating Biomolecular Recognition into Nanomechanics," Science, Apr. 14, 2000, 288:316-319; XP000971747.

Ho et al., "Thermal Conductivity of the Elements," J. Phys. Chem. Ref. Data, 1972, 1, 279-421.

Hoh et al,. "Quantized Adhesion Detected with the Atomic Force Microscope," J. Am. Chem. Soc., 1992, 114:4917-4918, American Chemical Society.

Lang et al,. "An artificial nose based on micromechanical cantilever array," Analytica Chimica Acta, Mar. 1999, 393:59-65; ZP000990018.

Lee et al., "Sensing Discrete Streptavidin-Biotin Intreactions with Atomic Force Microscopy." Langmuir, 1994, 10:354-357, American Chemical Society.

Levin, Yu, "Internal thermal noise in th LIGO test masses: A direct approach," Physical Review D, Jan. 15, 1998, 57(2):659-663, The American Physical Society.

Meiners et al., "Direct Measurement of Hydrodynamic Cross Correlations between Two Particles in an External Potential," Physical Review Letters, Mar. 8, 1999, 82(10):2211-2214, The American Physical Society.

Moy et al., "Intermolecular Forces and Energies Between Ligands and Receptors," Science, Oct. 14, 1994, 266:257-259, American Association for the Advancement of Science.

Roukes et al., "Nanoelectrochemical Systems," Technical Digest of the 2000 Solid-State Sensor and Actuator Workshop. Jun. 4-8, 2000, Nov. 8, 2000, 1-10; ZP002284418.

Sader, John Elie, "Frequency response of cantilever beams immersed in viscous fluids with applications to the atomic force microscope," Journal of Applied Physics, Jul. 1, 1998, 84(1):64-76, American Institute of Physics.

Sengers et al., "Improved International Formulations for the Viscosity and Thermal Conductivity of Water Substance," J. Phys. Chem. Ref. Data, 1986, 15, 1291-1314.

Viana, Mario B., "Small cantilevers for force spectroscopy of single molecules," Journal of Applied Physics, Aug. 15, 1999, 86(4):2258-2262, American Institute of Physics.

Whalen, Anthony D., "Detection of Signals in Noise," Chapter 1. Probability, 1971, 1-26, Academic Press, New York.

* cited by examiner

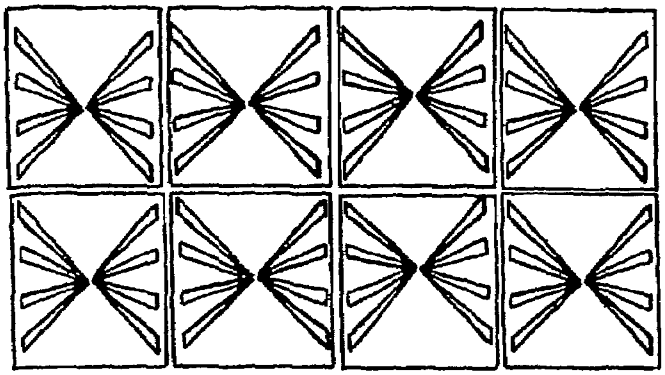
FIG. 13K
FIG. 13M
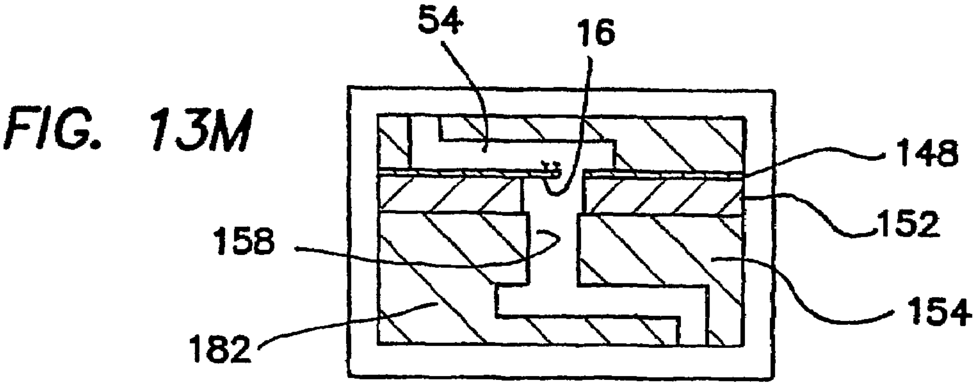
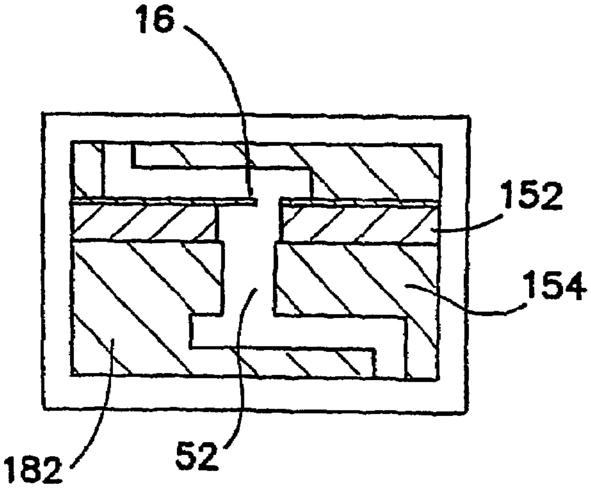
FIG. 13L

DYNAMICS BIONEMS SENSORS AND ARRAYS OF BIONEMS SENSOR IMMERSED IN FLUIDS

RELATED APPLICATIONS

The present application is related to U.S. Provisional Patent Application Ser. No. 60/379,710, filed on May 7, 2002; Ser. No. 60/379,660, filed on May 7, 2002; Ser. No. 60/379,645, filed on May 7, 2002; Ser. No. 60/379,552, filed on May 7, 2002; Ser. No. 60/379,711, filed on May 7, 2002; Ser. No. 60/379,543, filed on May 7, 2002; Ser. No. 60/379,643, filed on May 7, 2002; Ser. No. 60/379,708, filed on May 7, 2002; and Ser. No. 60/379,681, filed on May 7, 2002, which are incorporated herein by reference and to which priority is claimed pursuant to 35 USC 119.

FEDERAL SUPPORT STATEMENT

The U.S. Government has certain rights in this invention pursuant to Grant No. F49620-02-1-0085 awarded by the United States Air Force Office of Scientific Research (AFOSR).

INCORPORATION OF COPENDING APPLICATIONS

It is to be expressly understood that the present application incorporates by reference simultaneously filed applications serial no. (PAU.34), entitled, "An Apparatus And Method For Vacuum-Based Nanomechanical Energy, Force, And Mass Sensors"; and serial no. (PAU.35) entitled "A Method And Apparatus For Providing Signal Analysis Of A Bionems Resonator" as if set out in their entirety. Further the present application incorporates by reference U.S. patent application Ser. No. 10/138,538, filed on May 3, 2002 entitled, "An Apparatus and Method for Ultrasensitive Nanoelectrochemical Mass Detection"; and U.S. patent application Ser. No. 09/927,779, filed on Aug. 9, 2001, entitled, "Active NEMS Arrays for Biochemical Analyses" as if set out in their entirety.

BACKGROUND OF THE INVENTION

1. Field of the Invention

The invention relates to the field of fluidic bioNEMS devices and methods of operating the same.

2. Description of the Prior Art

There have been a number of recent advances in NEMS and in Chemical Force Microscopy (CFM). NEMS approaches have resulted in a family of cantilevers of small length and thickness that can resonate at high frequency with high Q. When operated in ideal conditions (low T, vacuum) these NEMS devices show unprecedented sensitivity. On a much larger size scale (AFM, CFM), work in several groups has been directed at analyzing the forces exerted by interactions between single molecules, ranging from hydrogen bonds and antibody-antigen interactions to covalent bonds. AFM cantilevers, decorated with biomolecules and interacting with derivatized surfaces or with derivatized magnetic beads, demonstrate forces of order 100 pN for an antigen-antibody interaction and ~1-10 nN for a covalent bond. These watershed experiments show the feasibility of measuring chemical events at the stochastic limit, but also offered evidence of the difficulty of harvesting this potential in a small, portable and robust device.

According to the invention what is needed is some way of reducing the size of the cantilever to NEMS dimensions to offer the needed temporal response, small volume and sensitivity to single molecules needed to build a device with single cell capability. Of course, placing a NEMS cantilever in solution and at room temperature will call for a revision of detection strategy from those usually employed for either CFM or NEMS. The fluid will damp the NEMS cantilever making resonance detection impossible, and the thermal energy of the solution will buffet the cantilever.

What is needed is some way to exploit these to potential difficulties as an integral part of the assay.

In contrast to conventional CFM what is needed according to the invention is an approach which will not attempt to measure the force of a single (or small number of) chemical bond by recording cantilever deflection.

What is needed is some type of design for a NEMS cantilever will allow detection of the presence of a chemical bond by the restriction it produces in the otherwise large thermally driven motion of the cantilever using an integral sensor.

What is further needed according to the invention is a means of using an array of BioNEMS cantilevers with systematically different chemical decorations offers both high reliability and sensitivity to concentration.

Further, according to the invention what is needed is some way of interpreting the "noise" of fluctuations as signal, and biology the opportunity of assembling and employing a useful and robust assay.

Microarray technologies have provided significant recent advances in analyzing protein receptors and their ligands, as well as in analyzing gene expression profiles. For example, microarrays of a few thousand targets have become a major technique used by the drug discovery industry. These microarrays are created by photolithography, by microstamping, or by microdotting, resulting in an array of spots (20-100□m) on a substrate. The array is typically read by superfusing a fluorescently labeled analyte, over the array and determining the amount of binding by scanning the array with a micro-fluorimeter. Although these approaches are becoming increasingly widespread, the large size of the reader instrumentation and the intrinsic limitations of the fluorescence analysis employed make them completely inappropriate for applications in which both portability and robust performance are required. Furthermore, they are single-use devices, hence they cannot easily accommodate applications that require continuous monitoring. Finally, the devices rely on significant volumes of analyte, making them ill-suited to the most powerful recent advances in drug discovery provided by combinatorial chemistry or to the most sensitive assays of gene expression.

Another goal of the proposed studies is to develop a new technology of biochips at the nanoscale (BioNEMS) that is capable of sensing the binding of single biological molecules to their receptors. A growing literature of chemical force microscopy (CFM) has shown that a modified AFM can be tailored to measure the binding force of interactions ranging from single hydrogen bonds and single receptor-ligand interactions to single covalent bonds. The range of these forces are well within the capability of AFM instrumentation to detect; however, an AFM cantilever in solution does not have the temporal response characteristics needed to permit the binding and unbinding of biological ligands and their receptors to be followed reliably. Perhaps even more significant is the substantial size of the equipment required for performing AFM/CFM, and the well-known sensitivity of AFM to air-borne and surface vibrations.

What is needed is some type of technology that has the same success as CFM in detecting the forces of single molecular interactions, but is scaled down to NEMS scale to permit it to respond rapidly enough to follow the binding and unbinding events. Given the size of the chemical forces, the most robust mode for the BioNEMS to operate will be to forsake direct measurements of the force of binding. What is needed according to the invention is some type of means for using the ongoing fluctuations in the position of the NEMS cantilever followed using integral sensors to obviate the need for the support equipment used in AFM.

BRIEF SUMMARY OF THE INVENTION

According to the invention the motions of the NEMS cantilevers will be used to follow binding and unbinding events. The basic idea is that a cantilever that is not coupled at its tip by a receptor-ligand pair will fluctuate in its position more dramatically than a cantilever that is restricted by a ligand-receptor pair. Strong ligand-receptor bonds can partially arrest the cantilever motion for considerable time (~$t_{on}$ for the ligand-receptor pair); even weak interactions will alter the statistics of cantilever motion.

Moving down to the small size of NEMS devices offers several significant advantages. "NEMS" in this specification is used to mean devices with at least one dimension which is equal to or smaller than one micron. It does not exclude the possibility that the "NEMS" device may have one or more other dimensions larger than one micron. Furthermore, as can be understood there is often no sharp line of distinction between the characterization of a device at or below one micron in size and one which is above one micron. The more meaningful significance to the term, "NEMS" that the device in question shares some characteristic with similar devices scaled to submicron sizes or which is unique to submicron devices or operation. As already mentioned the small size of the NEMS devices permit them to be dramatically more responsive to the kinetics of binding and unbinding. This high frequency response is critical to following the stochastic nature of receptor ligand interaction, most receptor-ligand pairs interact dynamically, binding, remaining engaged for times ranging from microseconds to seconds (depending on the exact receptor-ligand pair), and then releasing. High frequency response (~MHz) is critical if an assay is to follow biomolecular interactions. The ability to resolve the opening and closing of individual membrane channels in the patch-clamp (gigaohm seal) technology has revolutionized our understanding of the physical biochemistry underlying neuronal function; before the patch-clamp, experimenters could only attempt to decode molecular mechanism from recordings of huge populations of membrane channels. It is our belief that the analysis of biomolecules is presently in exactly the same state, limited by both the vast quantities of materials required and the smearing in time inherent in even the most sensitive assays. BioNEMS are thus poised by the invention to truly move our analysis of biomolecules to the stochastic limit.

One of the powers of this approach is that it exploits the thermal motion of the cantilever, normally a major limitation in AFM, as a driving force. Furthermore, the noise of cantilever motion becomes smaller as cantilever size is decreased. In addition, the small size of NEMS devices permits an array of detectors ($\geqq$500 cantilevers) to be constructed in a small active volume ($\leqq$100 pL). This latter advantage is of great significance, as it offers the promise of a technology for sensing the levels of RNA, proteins and second messengers present in single cells.

The BioNEMS approach of the invention offers a major reduction in the size and nature of the instrumentation needed for it to operate (in comparison to AFM/CFM). The sensor for the motion of the cantilever will be integral to the NEMS cantilever, which eliminates the size and density limits that would be imposed by the optical detection of cantilever motion used in AFM. This will permit the BioNEMS cantilevers to be much smaller and to be dramatically more closely packed than is practical in AFM.

As outlined in the section describing NEMS sensing below, integration of a piezoresistive transducer will offer sensitivity far greater than needed to record the NEMS cantilever motions in liquid water. As a result, with proper integration, the sensor, the detectors needed to follow cantilever motion, the logic needed to interpret the motions, and the circuitry needed to communicate the results can be packaged into a single device. In contrast to the promise of their names, current "DNA Chip" or "Proteomics Chip" technologies require bulky and heavy readers to interpret the binding of chemical species to a sensor package several centimeters in length and width. The BioNEMS approach outlined here offers the promise of package sizes consistent with the term "chip" (~DIP dimensions) and thereby offers a variety of applications that would be impossible or impractical by other approaches.

The goal of the proposed work is to exploit the thermally driven motion of the cantilever, and its modulation by receptor-ligand interactions. Knowledge of the physics of NEMS cantilevers in solution and of stochastic biochemistry will be used to interpret the motion of the cantilever. Thus, the construction of a working BioNEMS of this class requires a close collaboration between researchers working on NEMS fabrication, biologists working on the biochemical modification of device surfaces, physicists interested in the fluid dynamics of NEMS devices, and information scientists accomplished at extracting and analyzing data from arrays.

The BioNEMS research effort outlined here will have several thrusts, ranging from fundamental to applied science, and the development on new nanoscale fluidic technology. Our goal is to develop, understand and, thereby, to refine the techniques for the construction of BioNEMS and then demonstrate their novel uses.

Examples include:

Basic studies of the performance of NEMS in solution

Basic studies of single molecule chemistry

Cellular studies of hormones, growth factors and second messenger. The release of growth factors from cells is typically in too low of a concentration and too small a volume for direct analysis by traditional techniques.

Use of the BioNEMS as sensors for the output of combinatorial chemistry syntheses as a test in drug discovery efforts.

Use as a sensitive "gene chip" for the detection of DNA sequences, or as a sensor for biological hazards.

Use as a monitor of the concentration of environmental toxins.

The invention is defined as a submicron bioNEMS device comprising a support and a piezoresistive cantilever coupled to the support extending therefrom with a length I and having a width w and a tip, wherein the cantilever has a restriction portion of reduced width, b, and a length $I_1$, and a biofunctionalized portion at or near the tip. The restriction portion is comprised of multiple legs of reduced width, b, attached to the support. Preferably two legs are provided and are separated from each other by a distance of w−2b.

The bioNEMS device further comprises a source of bias current applied to the restriction portion of the cantilever and where the magnitude of the bias current is limited by a maximal acceptable temperature increase at the biofunctionalized tip. The maximal acceptable temperature increase at the biofunctionalized tip is approximately 1 degree K.

The invention is also an improvement in a piezoresistive bioNEMS device immersed in a fluid comprising at least one oscillating cantilever having a length I having a magnitude chosen to minimize background Johnson noise relative to signal strength generated by the piezoresistive bioNEMS device. In one embodiment the signal strength is based on thermomechanical noise levels of the piezoresistive bioNEMS device in the fluid. The piezoresistive cantilever has a width w, and a restriction portion of reduced width, b, wherein the reduced width, b, is chosen to reduce Johnson noise relative to the signal strength generated by the piezoresistive bioNEMS device.

The invention is further characterized as an improvement in a biofunctionalized bioNEMS device immersed in a fluid comprising a receptor disposed on the bioNEMS device for binding to a ligand of interest and a catalyst disposed on the bioNEMS device with the receptor to enhance binding rate coefficients of the receptor with the ligand of interest. The catalyst lowers the receptor-ligand binding activation energy. In one embodiment the receptor is designed by forced evolution to preferentially bind with the ligand of interest.

The invention is also defined as a submicron device comprising a source of a carrier signal, a support, a piezoresistive cantilever coupled to the support and extending therefrom, and an element disposed on the cantilever and electromagnetically coupled to the source so that the cantilever is driven by the carrier signal from the source. The element comprises a magnetic film disposed on the cantilever, and the source generates an electromagnetic signal coupled to the magnetic film.

Still further the invention is an apparatus comprising a plurality of NEMS resonators or transducers, each of the NEMS transducers generating an output signal; and means or circuit for processing the plurality of corresponding output signals from the plurality of NEMS transducers to obtain a collective output signal. The means averages the plurality of output signals so that the collective output signal is an average. The means determines if a predetermined fraction of the plurality of output signals are above a threshold within a predetermined time window. Each of the plurality of NEMS transducers is biofunctionalized and the means effectively increases ligand capture rates by only generating a collective output signal indicative of an increase ligand capture rate as compared to a single one of the NEMS transducers.

The invention is described as an apparatus operating in a fluid comprising a plurality of NEMS transducers immersed in the fluid forming an array of adjacent transducers, each of the NEMS transducers generating an output signal, the motion of two adjacent NEMS transducers being coupled to each through the fluid in which the adjacent NEMS transducers are immersed. A cross correlation of movement of a first and second NEMS transducer exists and comprises the two adjacent NEMS transducers, $C_{12}=<x_1(0)\ x_2(t)>$, as defined by $$\frac{d}{dt}C_{12}(t) = -k_B T X_{12}(t) \text{ for } t > 0$$

where $k_B$ is the Boltzman constant, T is the temperature of the fluid, t is time, and $X_{12}$ the "susceptibility" giving the displacement $x_2(t)$ of the second transducer for a force $F_1$ acting on the first transducer, such that an ensemble average for the position of the second transducer is defined by $$\langle x_2(t)\rangle = \int_{-\infty}^{\infty} X_{12}(t-t')F_1(t')dt'.$$

The invention is an apparatus operating in a fluid comprising a microfluidic flow channel for carrying a flow of the fluid, and at least one NEMS transducer disposed in the microfluidic flow channel so that a characteristic of the fluid is sensed by the NEMS transducer. The NEMS transducer is biofunctionalized and the characteristic of the fluid is sensed by the NEMS transducer is the presence or absence within the fluid of a ligand to which the NEMS transducer has been biofunctionalized.

The apparatus further comprises a plurality of the NEMS transducers, each of which is disposed in common in the flow channel. The apparatus further comprises a plurality of flow channels among which the plurality of NEMS transducers re distributed. The plurality of NEMS transducers are surface fabricated or membrane fabricated.

The invention includes a method of fabricating a bioNEMS device from a membrane comprising the steps of providing a heterostructure comprising a wafer layer, an etch stop layer on the wafer layer, a NEMS device layer on the etch stop layer, and a piezoresistive layer on the NEMS device layer. Trenches are etched through the wafer layer to the etch stop layer to define an area which will become a membrane in which the NEMS device will be defined. The etch stop layer is removed from the bottom of the trenches to the device layer to form the membrane. Conductive contacts are selectively formed on the piezoresistive layer of the membrane by electron beam lithography. Regions are selectively formed which will become biofunctionalized on the piezoresistive layer of the membrane by electron beam lithography. A NEMS device is selectively formed on the piezoresistive layer of the membrane by electron beam lithography which include the region which will become biofunctionalized. The membrane is selectively plasma etched to remove unmasked portions to define a suspended NEMS device. A flow channel is selectively molded in an elastomeric layer disposed around the membrane. Selected regions are biofunctionalized on the NEMS device.

The step of providing a heterostructure further comprises polishing the wafer layer to promote adhesion to the elastomeric layer and thinning the wafer layer. The step of selectively plasma etching the membrane to remove unmasked portions to define a suspended NEMS device comprises selectively vertically plasma etching away unmasked portions of the NEMS device layer. The step of selectively molding a flow channel in an elastomeric layer disposed around the membrane comprises selectively disposing a photoresist layer to define the flow channel, disposing an elastomeric layer on the selectively disposed photoresist layer, and removing the photoresist layer to define the flow channel.

The invention discloses a NEMS device for operating in a fluid comprising a resonating member having a tip immersed in the fluid, a linking molecule attached to the tip; and a fluffball attached to the linking molecule and providing a damping force to dissipate noise applied to the member from the fluid.

The invention also includes methods for operating the NEMS devices disclosed above.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

BRIEF DESCRIPTION OF THE DRAWINGS

FIGS. 13*a*-13*m* are a series of diagrams illustrating a method for fabricating a bioNEMS fluidic sensor from a membrane.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

The illustrated embodiment is directed to the constraints upon the level of current bias that can be applied to a piezoresistive BioNEMS device in fluid. The force sensitivity attainable clearly hinges on the maximum level of current bias that is tolerable, given that the responsivity is proportional to bias current, R=I G. The largest practical level of bias current is determined by the maximum temperature rise in the BioNEMS which is deemed acceptable.

Figure 12A:
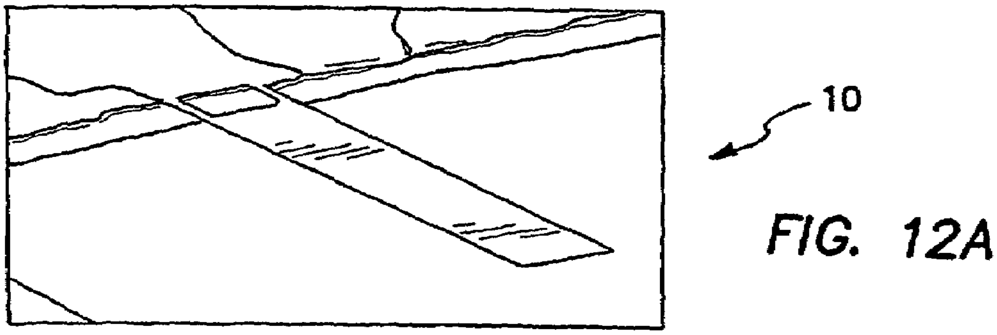
FIG. 12*a* is a scanning electron microscopic photograph of a bioMEMS transducer.
Figure 12B:
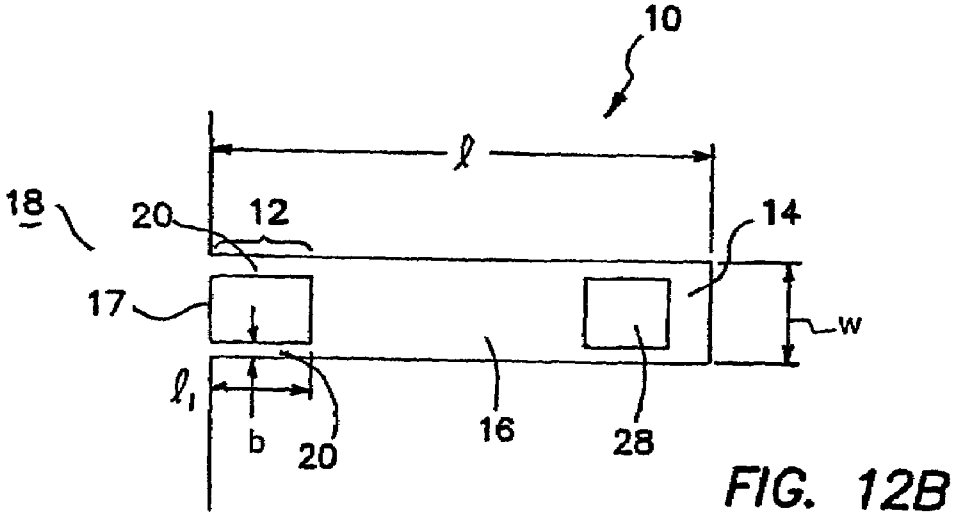
FIG. 12*b* is a diagram of the top plan view of the transducer of FIG. 12*a*.

For the purposes of illustration the bioNEMS transducer or cantilever 10 shown in perspective view in the microphotograph FIG. 12*a* and in the top plan view diagram of FIG. 12*b* shall be assumed, which can be analogized as having the form of "a diving board with a cutout at its base". However, it is to be expressly understood that the geometry of the transducer 10 is to be entirely general and includes any type cantilever, doubly clamped beam, paddle or any other submicron oscillating structure. The geometry of the device 10 causes maximization to occur predominantly within a constriction region 12 comprised of one or more legs 20 of width b, as shown in FIG. 12*b* which region 12 allows for enhanced or variably designed flexural stiffness of cantilever 16 without restricting the fluidic damping characteristics of cantilever 16 dependent on its over length I and width w. It is also to be understood that cantilever 16 will have conventional electrodes (not shown) provided whereby a conventional external measurement circuit (not shown) providing a bias current may measure the change in piezoresistivity of legs 20 as they flex. In addition, an external driving force may or may not be applied in a conventional manner to cantilever 16 depending on the application and design choice.

In the preferred embodiment there are two legs 20. We assume that a temperature rise of order 1 K is tolerable at the biofunctionalized tip 14 of the cantilever 16, which has a length, I, a width, w, and a thickness, t, resonant frequency in vacuum $\omega_0/2\pi$ and force constant K.

We treat the problem as one dimensional, with the constricted region a beam 16, of length $I_1$ and cross sectional area A, heat sunk at the supporting end 17 to supporting substrate 18. In the illustrated embodiment, cantilever 16 is made of silicon and assumed to be immersed in water, but any nanomachinable material may be employed and any ambient fluid may be contemplated. The distance x is measured from the connection of cantilever 16 to support 17 towards its tip 14. For x>$I_1$, a rough estimate of the heat loss to the water or fluid in which device 10 is immersed may be obtained through the relationship $$\kappa_{\mathrm{Si}} A \frac{d^2 T}{dx^2} = \kappa_{\mathrm{H_2O}} P \nabla T$$

where P is the perimeter around cross-sectional area A of the beam 16. Estimating $\nabla_n$ T~T/w, and $$\frac{d^2 T}{dx^2} \sim \frac{2(w+t)\kappa_{\mathrm{H_2O}}}{\kappa_{\mathrm{Si}} t w^2}$$

where $k_{Si}$=1.48×I$0^2$ W/mK is the thermal conductivity of silicon and $\kappa_{H_2O}$=0.607 W/mK is the thermal conductivity of water. In the dissipative region x<$I_1$ we have $$\kappa_{\mathrm{Si}} t b \frac{d^2 T}{dx^2} \sim -I^2 R + 4(b+t)\frac{T}{b}\kappa_{\mathrm{H_2O}}.$$

As boundary conditions, we have that the temperature is continuous at $I_1$, as is the heat flux; and the temperature must monotonically decrease for $x>I_1$.

We consider the three illustrative devices 10 from Table 1. For the first cantilever 16, this simple thermal conductance calculation indicates that a 1 K temperature rise at the biofunctionalized tip 14 is attained with a steady-state bias current I/=250 μA., leading to a power dissipation of roughly 10,670 μW. The maximal temperature rise of 12 K occurs within the constricted region 18, approximately 2.3 μm from the edge of substrate 18. For this bias current, the first device yields a responsivity R=/I G of about 8 μV/nm.

For the second cantilever 16 in Table 1 we allow the same 12K maximal temperature rise in the constricted region 12, this coincides with a temperature rise of 0.04K at the tip 14 and occurs for a current of 75 μA. For this device 10 we expect a gauge factor $G=5.2\times10^{9}$ Ω/m. Hence the expected responsivity is 390 μV/nm.

Finally, for the third cantilever 16 in Table 1, using a 12K maximal temperature rise in the constricted region 12 and 0.04K at the tip 14, we can allow a current of 22 μA. For this device we anticipate $G=5.3\times10^{10}$ Ω/m. Hence the expected responsivity is 1.2 mV/nm.

TABLE 1

| # | t | w | l | $l_1$ | b | $\omega_0/2\pi$ | K |
|---|---|---|---|---|---|---|---|
| 1 | 130 nm | 2.5 μm | 15 μm | 4.0 μm | 0.6 μm | 0.51 MHz | 34 mN/m |
| 2 | 130 nm | 300 nm | 10 μm | 2.0 μm | 100 nm | 1.3 MHz | 20 mN/m |
| 3 | 30 nm | 100 nm | 3 μm | 0.6 μm | 33 nm | 3.4 MHz | 3.0 mN/m |

Scaling of Fluidic Coupling in BioNEMS

For applications in which device 10 is driven by fluid-coupled thermomechanical noise in the fluid in which it is immersed, it is beneficial that this signal be maximized relative to the background Johnson noise in device 10. The relative strength of these two sources of thermal noise is determined by the cantilever's 16 dimensions. These dimensions enter both into the magnitude of the fluidic damping which determines the spectral density of the fluid-coupled thermomechanical noise in the force domain and into the response function of the cantilever 16 (through the damping, effective mass, gauge factor, spring constant and allowed current for the same amount of heating at the tip).

Figure 1:
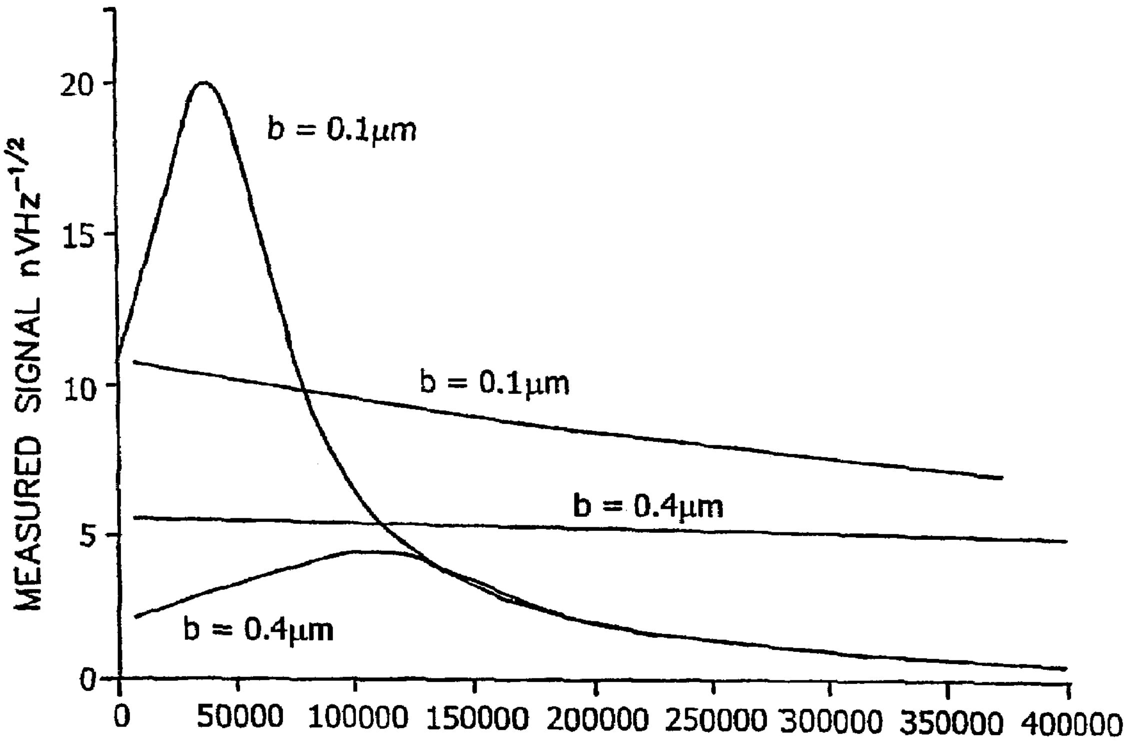
FIG. 1 is a graph of the observed improvement in the strength of the fluid coupled thermomechanical noise relative to the Johnson noise with all other dimensions fixed.

For fixed thickness, t, a substantial improvement in signal strength may be obtained by decreasing the width of the cantilever legs 20 as illustrated in the graph of FIG. 1 where measured signal strength of device 10 in $nV/Hz^{1/2}$ is graphed against frequency of the thermomechanical noise and Johnson noise for devices with b=0.4 μm and b=0.1 μm. Increasing the total length I and width w of the cantilever 16 increases the coupling to the fluid, increasing both the fluidic damping and the cooling efficiency; also leading to an improved signal-to-noise ratio.

Figure 2:
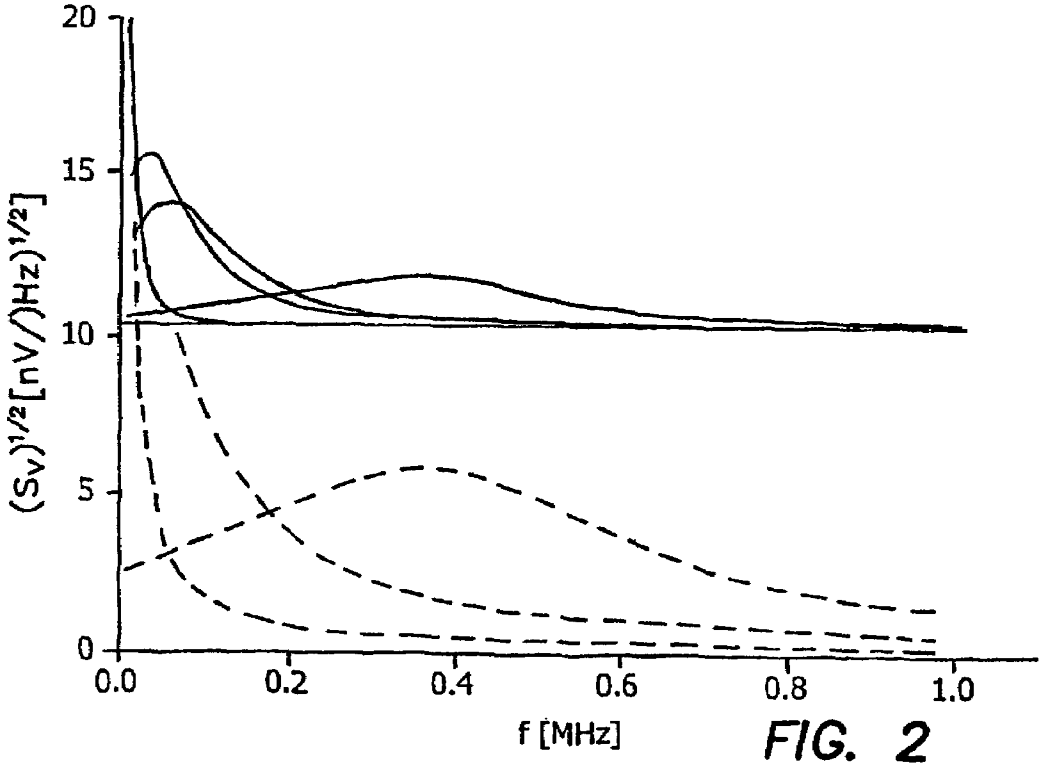
FIG. 2 is a graph of the fluid damped thermomechanical noise.

The effect of increasing the length I of cantilever 16 is shown in the graph of FIG. 2, for cantilevers 16 of different lengths I as shown in the tabular inset with b=0.1 μm, t=130 nm, and w=5 μm in common among each example. The ambient fluid was diethylene glycol. FIG. 2 is a graph of the fluid damped thermomechanical noise, which is predicted to increase relative to the background Johnson noise as the cantilever length is increased. For a length of 35 μm, the fluid damped thermomechanical noise has a peak an order of magnitude larger than the background Johnson noise. For each cantilever length, the bias current was chosen such that the estimated temperature rise at the tip 14 not exceed 1° C. and that at the point of maximal temperature in the legs 20 did not exceed 50° C. The bias currents used and estimated temperature rises are summarized in Table 2.

TABLE 2

| l | I | $\Delta T_{tip}$ | $\Delta T_{max}$ |
|---|---|---|---|
| 15 μm | 115 μA | 1° C. | 8° C. |
| 18 μm | 140 μA | 1° C. | 12° C. |
| 20 μm | 160 μA | 1° C. | 16° C. |
| 25 μm | 205 μA | 1° C. | 26° C. |
| 35 μm | 285 μA | 0.6° C. | 50° C. |
| Diethylene Glycol | | | |
| 35 μm | 140 μA | 1° C. | 15° C. |

Figure 3:
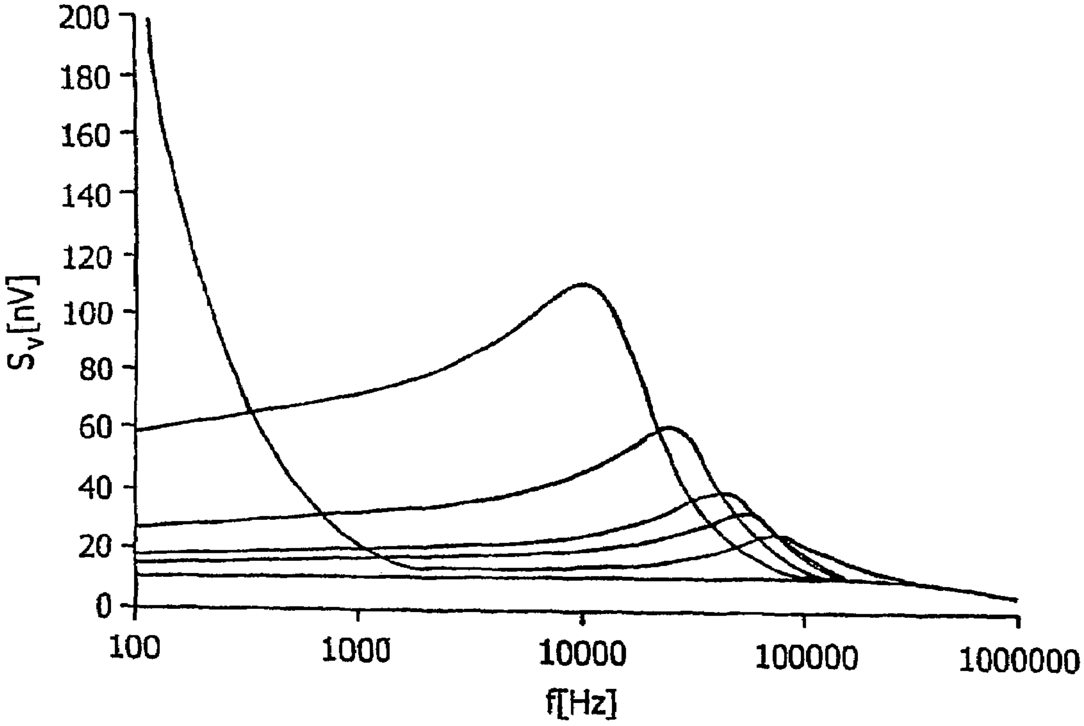
FIG. 3 is a graph of the expected signal in several liquids for a bias current of 250 μA, for a cantilever with b=O0.6 μm, t=130 nm, w=2.5 μm, I=15 μm and $I_1$=0.6 μm.

In addition to the dependence on the cantilever dimensions, it should also be noted that the magnitude of the fluid-coupled thermomechanical noise is dependent on the fluid viscosity. FIG. 3 shows the expected signal in the voltage domain for the Johnson noise and thermomechanical noise for a cantilever 16 with b=0.6 μm, t=130 nm, w=2.5 μm, I=15 μm and $I_1$=0.6 μm and a bias current of 250 μA for fluids with a range of different viscosities corresponding to water, diethylene glycol, glycerol, and ethylene glycol.

Enhancing Receptor-Ligand Reaction Probabilities

Figure 4:
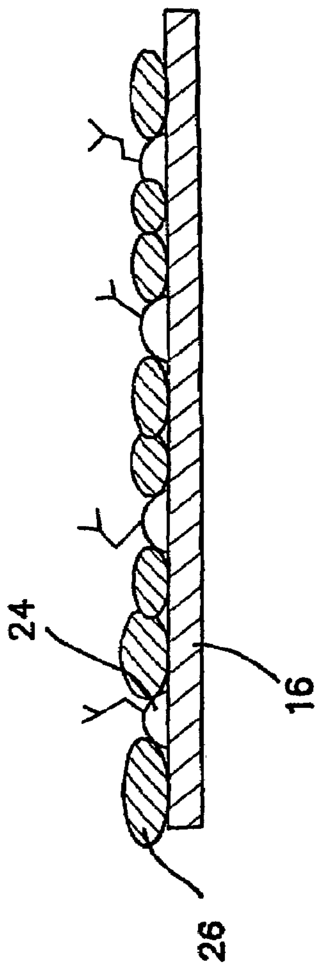
FIG. 4 is a diagrammatic side elevational view of the cantilever in microscopically enlarged scale.

In one embodiment, device 10 is biofunctionalized by having bioreceptor molecules 24 attached to or near tip 14 of cantilever 16 as diagrammatically shown in FIG. 4. Since one of the fundamental features of NEMS device 10 is the use of biological receptor molecules 24 attached to a "functionalized" region of an elastic cantilever 16, it is important that the receptor-ligand binding reaction have the highest possible rate coefficient (reaction probability) for the target ligand 22 of interest. However, it is well known that biologically expressed receptor molecules 24 do not in general have the highest possible binding rate coefficients for their target ligands, since evolution does not select for this attribute. Thus it will be useful to examine various methods for enhancing the binding rate coefficients for receptors 24 of interest in applications of the NEMS device 10.

One possible approach is to use the equivalent of catalyzed reaction by finding specific molecules which, when in close association with a particular specie of receptor 24, lower the receptor-ligand binding activation energy. Since rate coefficients, and thus reaction probabilities, are very sensitive to activation energy, e.g. have an exponential dependence, lowering this energy by even relatively small amounts yields large increases in the binding rate coefficients. Thus, the idea here is to first attach a layer of these "catalyst" molecules 26 to a small functionalized region 28 of the cantilever 16, and then attach the receptors 24 specific to the target ligand 22 of interest. The basic concept of this approach is shown in FIG. 4. The choice a catalyst in any given instance would be dictated by the ligand-receptor pair according well known principles.

A second and probably viable approach is to design the receptor molecules 24 whose binding rate coefficient is maximized with respect to a specific ligand 22 of interest. The term, "design" is understood here to mean that one uses forced evolution, biochemical techniques to select for genes that express the desired receptor 24 with higher and higher binding affinities for the chosen ligand 22 as one goes through multiple rounds of "evolving" the gene. This is usually accomplished by inserting multiple copies of the gene for a receptor 24 of interest into the genome of a particular bacterium so that the bacteria will express this receptor on their cell surfaces.

Binding affinity assays are then carried out on the first generation of bacteria, and only those with the highest binding affinities are kept for the next round of the "evolutionary" cycle. Prior to starting the next cycle, variations of the receptor genes a created either through point mutations, or more efficiently by "DNA-shuffling". These cycles are then repeated until it becomes clear that no further increase in binding affinity is possible. One might expect to achieve at least an order of magnitude increase in the binding rate coefficients for particular receptor-ligand pairs by utilizing this technology.

Non-Specific Ligand Binding Effects

Figure 5:
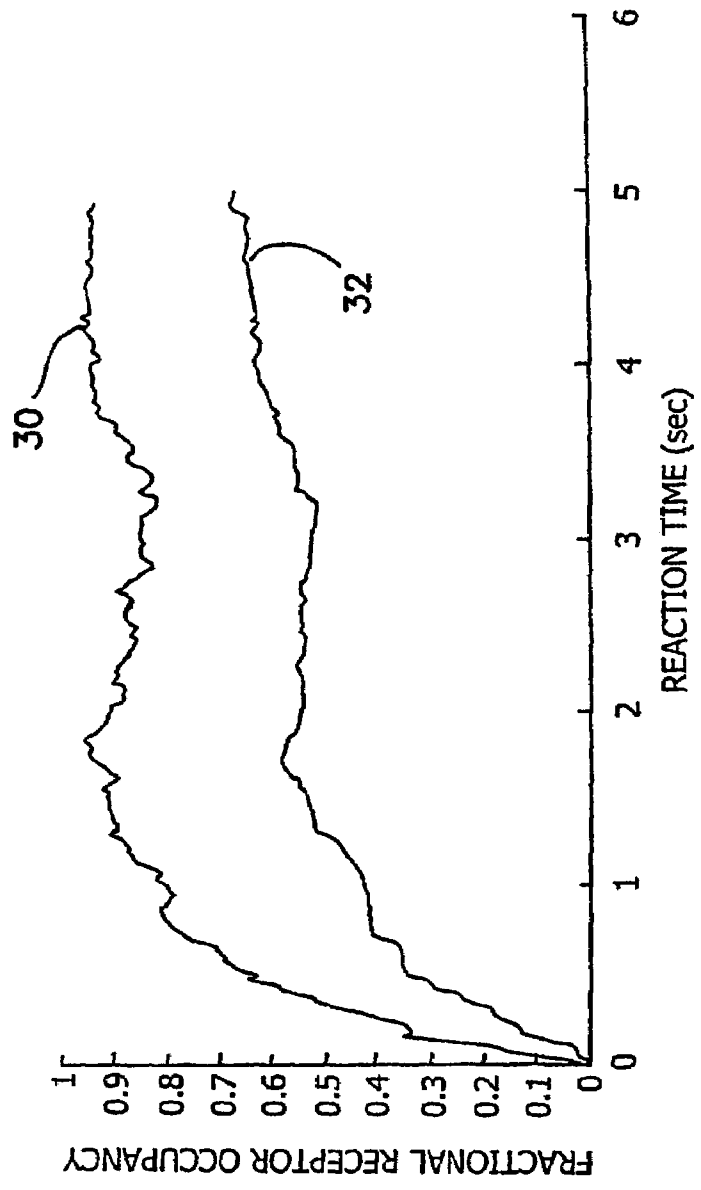
FIG. 5 is a graph of the fractional receptor occupancy as a function of nonspecific binding events.

FIG. 5 is a graph which shows an example of the possible effects of "background" non-specific binding on the response of NEMS cantilever 16. The curve 30 is the fractional occupancy of functionalized sites 28 by target ligand 22, while curve 32 represents the fractional occupancy by both target 22 and background ligand molecules 32. The conditions used were: (1) 1000 target ligand molecules 22; (2) 100 receptor molecules 24; and (3) 10,000 background ligand molecules 32; with a non-specific binding affinity of 200 times less than for the target ligand molecules 22. The effects of non-specific binding competition for receptors 24 could be significant for device 10 as shown in FIG. 5.

Use of Multiple Cantilevers for Signal Generation in BioNEMS

Figure 6:
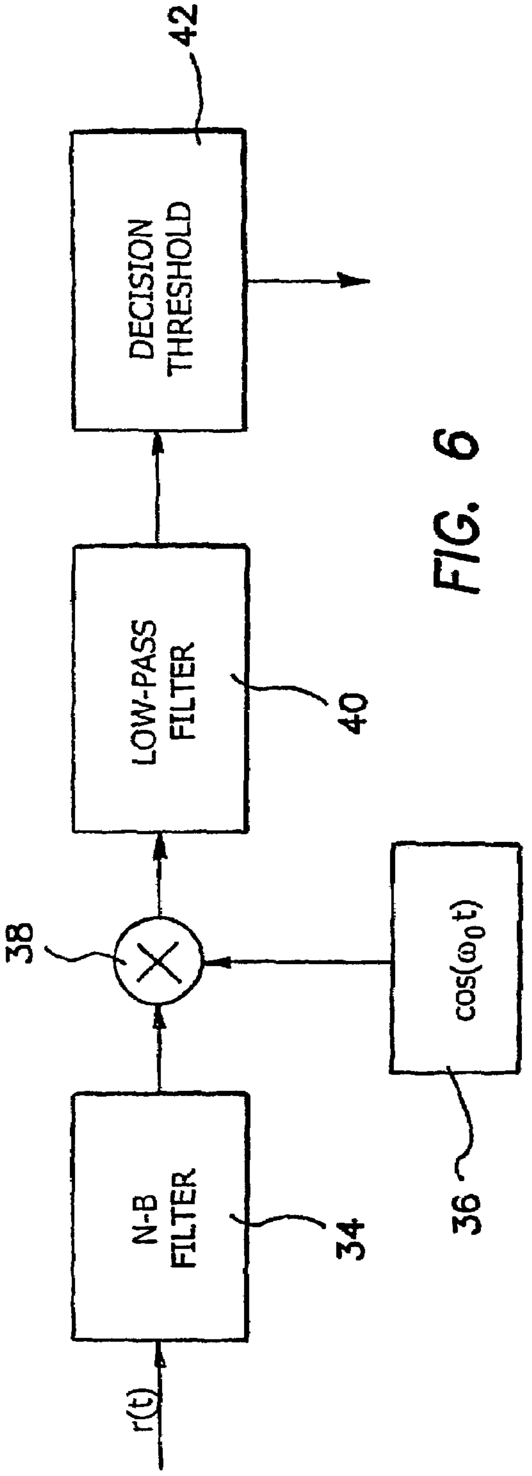
FIG. 6 is a diagram of a detector known as a "phase-detector" or "lock-in amplifier", or a correlation receiver.

The case of single undriven cantilevers 16 for biomolecule detection has been analyzed in detail copending patent application entitled, A METHOD AND APPARATUS FOR PROVIDING SIGNAL ANALYSIS OF A BIONEMS RESONATOR, Ser. No. 10/502,466, simultaneously filed herewith and which is incorporated herein by reference. There we analyzed the expected detection performance for several driven two-cantilever systems. In the illustrated embodiment here we explore some general issues related to the use of multiple cantilevers in BioNEMS devices 10. We approach this analysis from the standpoint of signal "design"; which is to say that we are looking for device configurations that will produce the optimum signal with respect to detection performance. Such a signal is given by $$r(t)=A\cos(\omega_0 t+\theta)+n(t), \qquad 1.1$$

where A is the amplitude of the signal, oscillating with frequency $\omega_0$; and n(t) is a zero-mean Gaussian noise process with variance $\sigma^2_n$. Now, if both A and $\omega_0$ are deterministic, i.e., not subject to fluctuations, then the optimum detector is known to be the so called "phase-detector" or "lock-in amplifier", a block diagram of which is shown in FIG. 6. In communications theory such a detector is called a correlation receiver. Thus, we will look at device configurations that allow us to inject a "carrier" signal, at a frequency of $\omega_0$, such that target ligand binding events will "modulate" this carrier, i.e., modify the value of A. The correlation detector of FIG. 6 is comprised of a narrowband filter 34 which takes its input, r(t), from device 10. A reference signal from oscillator 36 is mixed by mixer 38 with the output of filter 34. The mixed filtered signal is input into low pass filter 40 and then coupled to a thresholding and decision circuit 42, which determines first if the signal is qualified as a valid or information-bearing signal and then if qualified a decision algorithm is implemented to determine if device 10 has or has not detected the ligand-receptor interaction of interest. These circuits may be implemented in analog or digital signal processors or computers as controlled by hardware design, firmware or software as devised by conventional design options.

Figure 7:
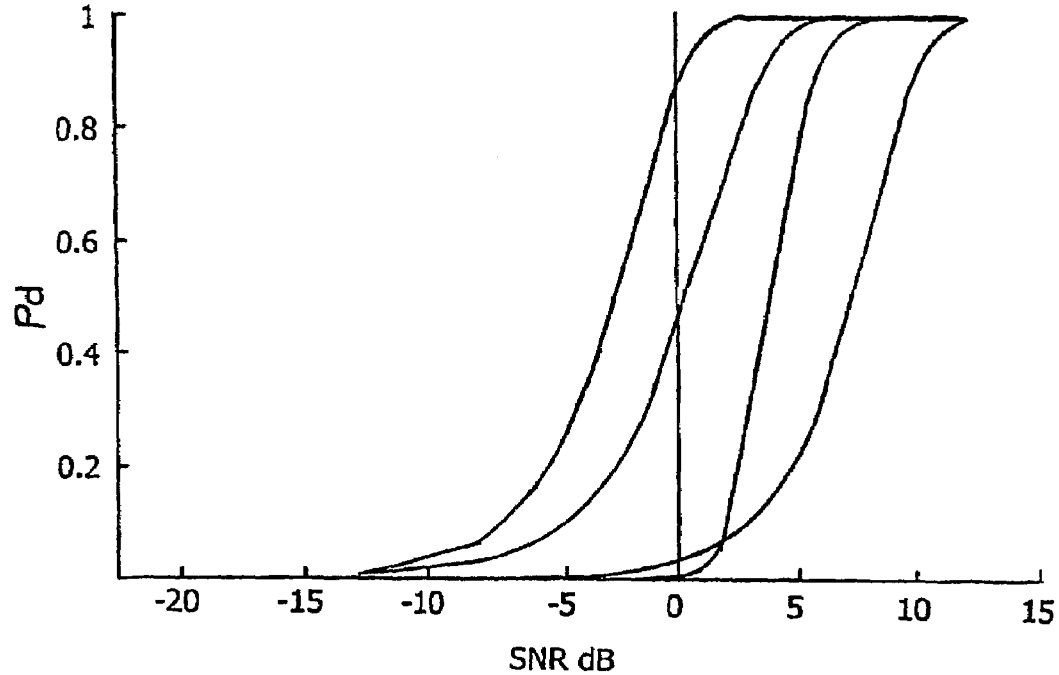
FIG. 7 is a graph illustrating detector performance Pd as a function of SNR.

We must deal with a relatively harsh constraint however, which is the severe loss of performance, if either the amplitude, A, or the phase, θ, of the signal are subject to significant random fluctuations. This loss of performance is illustrated in FIG. 7, where Case A is the "no random fluctuation" case; Case B is where there are random amplitude fluctuations; and Case C is the case where there is loss of phase information through random fluctuations. The case labeled "Chopper" is the performance of a single, undriven cantilever 16 using stochastic detection with multiple-sample summation as disclosed in the above incorporated referenced copending application. The method of injecting a carrier signal and "coupling" it to ligand-receptor binding events thus becomes a material consideration to obtain meaningful measurements.

Figure 8A:
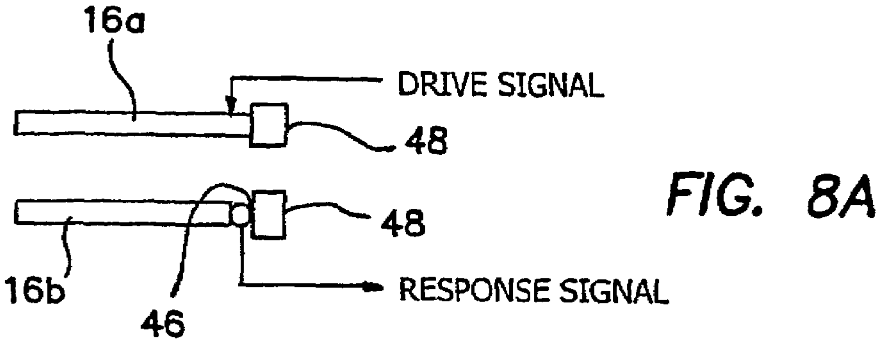
FIG. 8*a* is a diagrammatic top plan view of a double cantilever system.

FIGS. **8*a*-8*c* show two possible embodiments that can generate signals of the form of Eqn. 1. In FIG. 8*a* carrier injection is achieved by mechanically driving an unfunctionalized cantilever 16*a* with no receptors at a fixed frequency, $\omega_0$, and amplitude. The functionalized cantilever 16*b* responds to the driver 16*a* through fluid dynamic coupling of the fluid in which the device 10 is immersed. The driven cantilever 16*b* has a piezoresistive portion 46. Both cantilevers 16*a* and 16*b* are connected to supports 48, which in turn may be connected to substrates 44 or 50**.

Figure 8B:
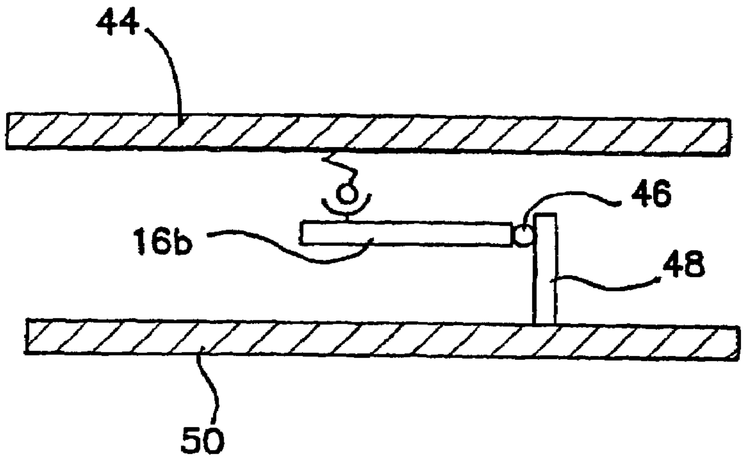
FIG. 8*b* is a diagrammatic side cross-sectional view of the system of FIG. 8*a*.
Figure 8C:
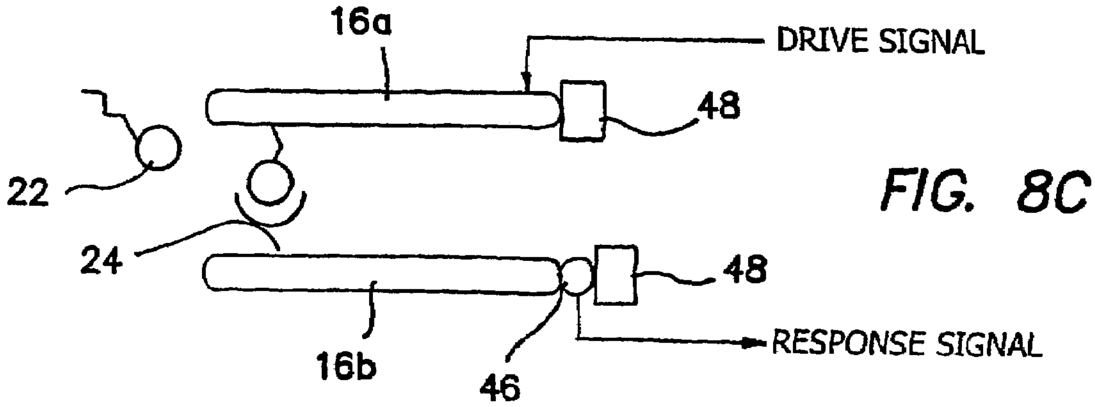
FIG. 8*c* is a diagrammatic top plan view of another embodiment wherein the cantilevers are ligand coupled.

In FIGS. **8*a*-8*c* the "no signal" case is where the cantilever 16*b* is constrained not to move significantly by "tacking" it to the substrate 44; the presence of "free" target ligand 22 results in breaking this condition through competitive binding. Note that the side-by-side arrangement of FIG. 8*a* is not the preferred configuration. As a practical matter it is better to have the two cantilevers opposed, i.e., tip-to-tip. FIG. 8*c* is a slightly different version of FIGS. 8*a* and 8*b*, where the no-signal state has the two cantilevers 16 and 34** mechanically coupled through a ligand-receptor binding arrangement. Again, presence of free target ligand disrupts this state through competitive binding, resulting in loss of a coherent signal.

Although we are discussing multiple cantilevers **16*a* and 16*b*, it should be pointed out that we can achieve very efficient carrier injection using a single cantilever 16 which has a small area 28 plated with a magnetic film; the external carrier signal source 36 is then generates a driving signal and is magnetically coupled to the cantilever 16 to obtain "constant" amplitude, constant phase oscillation of the cantilever beam 16**. In fact, this approach probably allows us to satisfy the parameter fluctuation constraint better than any other. The coupling may also be extended to electrostatic couplings using a dipolar or paraelectric film.

A different use of multiple cantilevers 16 is to utilize an array of N identical undriven cantilevers in either an averaging mode or a coincidence mode. In the averaging mode we simply use the N outputs to obtain a $\sqrt{N}$ improvement in our estimate of the variance. In coincidence mode, we use the constraint that some fraction of the N outputs must be above a threshold value within a fixed time window to be considered a "signal present" event. In both cases the method of using multiple cantilevers seeks to improve the ligand capture rate by increasing the number of available receptors 24.

Reducing Fluidic-Induced Correlated Fluctuations

Although the study of the single cantilever 16 in the fluid is quite well developed, there has been little attention paid to the fluid coupling of arrays of cantilevers 16. The fluid disturbance produced by the vibrating cantilever 16 is long range, falling off only as the inverse power of the separation distance between cantilevers 16. Moving one cantilever 16 will produce motion in the other cantilevers 16 through the viscous drag, or a fluidic coupling between the two cantilevers. There will correspondingly be a correlation of the stochastic motion of the cantilevers 16, since the stochastic force due to the molecular collisions on one cantilever 16 will induce motion of the second cantilever 16 through this coupling.

This connection is made quantitative through fluctuation dissipation theory. The fluidic-induced correlated fluctuations will tend to obscure the correlations induced by a molecule tethered between the cantilevers 16, making the detection and characterization of biomolecules using this scheme harder. It is important therefore to understand the fluidic induced correlations in the absence of biomolecules, and design geometries and protocols to minimize them.

Recent experiments by Meiners and Quake on laser-tweezer controlled spherical beads provide a first indication of the results to be expected. See J. C. Meiners et. al., *Direct Measurement Of Hydrodynamic Cross Correlations Between Two Particle In An External Potential*, Phys. Rev. Left. 82, 2211 (1999). These two authors studied the correlations induced by the fluid interaction of two 1 μm latex beads with separation, about 3-10 μm. They find a strong anticorrelation of the spheres with a maximum anticorrelation approaching the mean square displacement of a single sphere for the closest separation (3 diameters) that they investigated. This suggests a strong fluidic coupling that is hard to eliminate. However, the flow around a long cantilever 16 has quite different properties than the flow around a sphere, and this suggests a strategy for minimizing the fluidic correlations.

The low Reynolds number flow around a moving sphere is everywhere in phase with the motion of the sphere and falls off as 1/r. A simple model of our cantilevers 16 is to approximate them as cylinders, long compared to the radius. In this case the Stokes results for the flow around infinite cylinders can be used. The flow around an oscillating cylinder is more complicated than for spheres There is, in fact, no solution independent of Reynolds number for small values of the Reynolds number, and there are nontrivial frequency and distance dependent phase relationships between the velocity of the fluid and the velocity of the cylinder, varying on a distance scale of a few times $aR^{-1/2}$. Here a is the cylinder radius which we set to the cantilever width, and $R=\omega a^2/4v$ is the Reynolds number, with ω the frequency and v the kinematic viscosity of the fluid.

Figure 9:
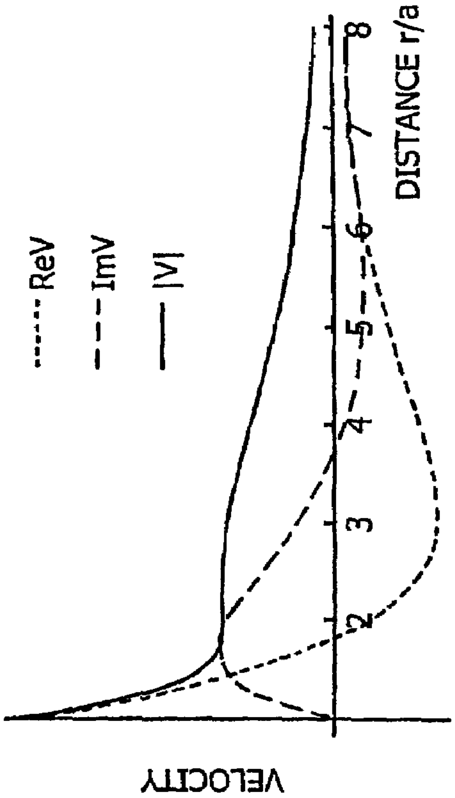
FIG. 9 is a graph of the fluid velocity component parallel to an oscillating cantilever as a function of distance, r.

For BioNEMS cantilevers 16, R is typically about unity. This velocity field is responsible for the motion of the second cylinder, so that there is a separation and frequency dependence to the motion of the second cylinder induced by the force on the first cylinder. Through the fluctuation-dissipation theorem, which states the fluctuations present in a system is proportional to the damping in the system, this gives us a separation and frequency dependence to the noise correlation. A plot of the velocity field as a function of the distance r/a from the cylinder axis in FIG. 9 shows in fact that the different quadratures of the velocity field have null points at different distances, suggesting that it might be possible to find parameters (cylinder separation/radius and frequency) corresponding to null points in the one or other phase of the fluid induced correlated noise. FIG. 9 shows the fluid velocity component parallel to the velocity of an oscillating cantilever 16 as a function of the distance r in units of the cantilever width a for a Reynolds number R=1. Note the nontrivial phase relationship given by the real (in phase) and imaginary quadrature components, and the null points of the different quadrature components.

A calculation of the correlations allowing design optimization proceeds as follows. The precise relationship between the cross correlation $C_{12}=\langle x_1(0)\ x_2(t)\rangle$ between the displacements of the two cantilevers and the deterministic fluidic coupling between the cantilevers is $$\frac{d}{dt}C_{12}(t) = -k_B T X_{12}(t) \text{ for } t > 0 \qquad 4.1$$

where $X_{12}$ is the "susceptibility" giving the displacement $x_2(t)$ of the second cantilever 16 for a force $F_1$ acting on the first cantilever 16

$$\langle x_2(t)\rangle = \int_{-\infty}^{\infty} X_{12}(t-t')F_1(t')dt' \qquad 4.2$$

The angular brackets denote an ensemble average, emphasizing again that a deterministic estimate, calculation, or experiment enables the stochastic motion to be quantified. The susceptibility $X_{12}$ can be calculated from the Stokes velocity field plotted in FIG. 9, and so the noise correlations can be predicted, although not presented here.

Merging NEMS to Microfluidics

Figure 10:
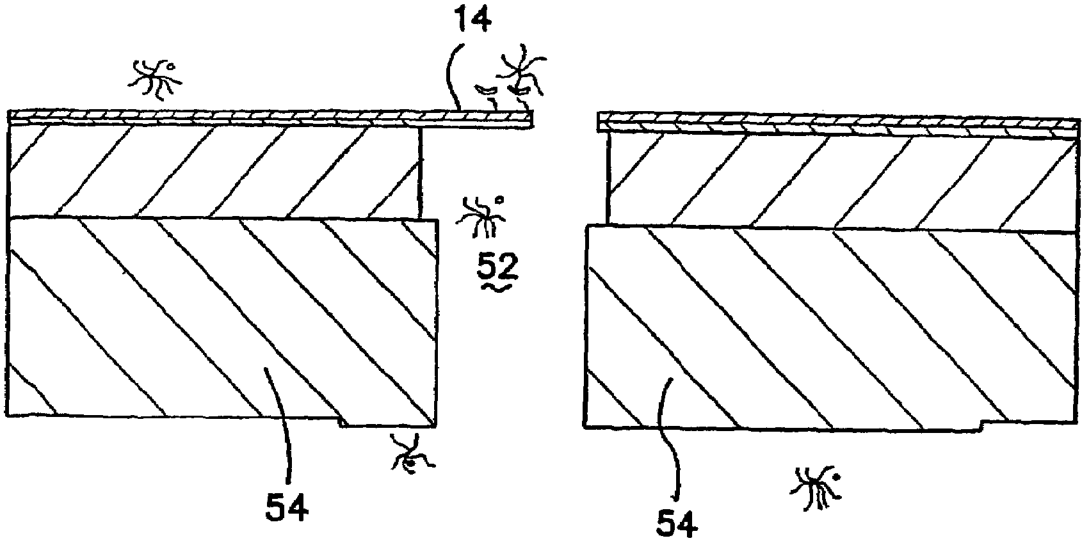
FIG. 10 is a cross sectional schematic side view of a piezoresistive cantilever coupled to a microfluidic flow channel
Figure 11A:
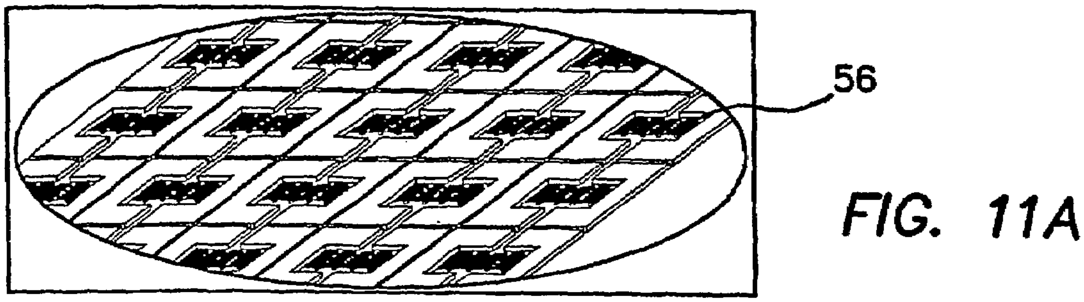
FIGS. 11*a*-11*c* is a diagrammatic perspective view in increasing magnification of the array of cantilevers shown in FIG. 10
Figure 11B:
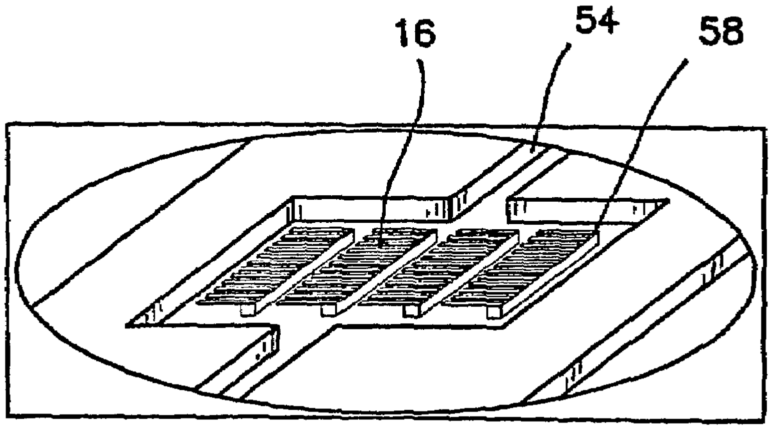
Figure 11C:
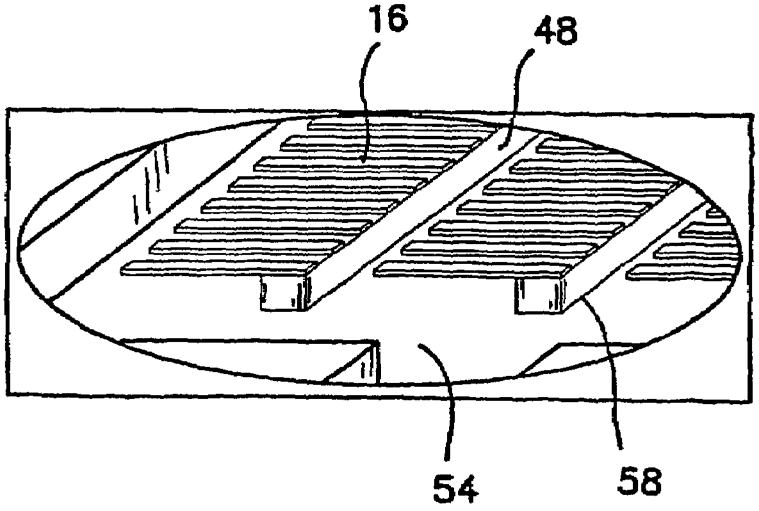

FIG. 10 shows a schematic of a cross section of a device 10 with a cantilever 16 coupled to a microfluidic flow channel 52. The region etched through the wafer 54 forms part of the final flow channel. An entire array of cantilevers 16 can be fabricated within a single flow channel 54. It is also possible to have multiple channels 54 with different devices 10 in different channels 54 depending on the desired application. It is also possible to surface fabricate the flow channels 54 directly in the silicon. This is shown schematically for an array 56 of devices in FIGS. 11*a*-11*c* which are three perspective views in increasingly enlarged scale showing a plurality of cantilevers 16 supported on parallel supports 48 forming rows of parallel cantilevers 16 in a single flow chamber 58 communicated with an inlet and outlet flow channel 54.

Fabrication of a BioNems Membrane Based Device

FIGS. 13*a*-13*g* show a flow diagram schematically depicting the steps involved in the fabrication of membrane-based BioNEMS devices 10. Fabrication of these devices begins with the side cross-sectional view of FIG. 13*a* with a silicon device layer 148 on insulator wafer 152, 154, such as a 375 nm $SiO_2$ layer 152 on a 675 μm Si layer 154. The buried oxide layer 152 must be thick enough to serve as a stop layer in the etching step through the back of the wafer 154. The Si device layer 148 should be of the desired thickness for the undoped portion of the silicon cantilever between 20 nm and 100 nm for most of the devices under consideration. In the illustrated embodiment an 80 nm Si layer 148 is disposed beneath a 30 nm heavily doped Si layer 150. The resistivity of layer 148 should be high relative to that of the heavily doped layer 150 which will be grown. (10 Ωcm is sufficient).

The backside of the wafer 154 is polished. This is necessary for the adhesion of an elastomeric material thereto in which microfluidic channels 52 will be defined as described below. The wafer 154 may be thinned at the same time which serves both to decrease the ultimate volume of the flow channel 52 and reduce the necessary thickness through which one must etch in a later etching step. A final wafer thickness of 300 μm is reasonable to maintain structural integrity of the wafer 154 while reducing the unnecessary material.

Next a layer of heavily boron doped silicon layer 150 is epitaxially grown on the top surface of layer 148, which layer 150 will form the conducting layer of the piezoresistor which forms part of the NEMS device 10. For most of the devices 10 this layer 150 is between 7 nm and 30 nm thick. The resistivity must be low compared to that of layer 148 below. A doping level of $4\times10^{19}$ $cm^{-3}$ is typical.

Figure 13A:
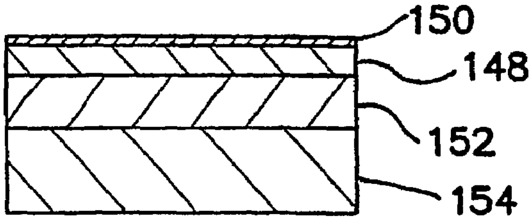
Figure 13B:
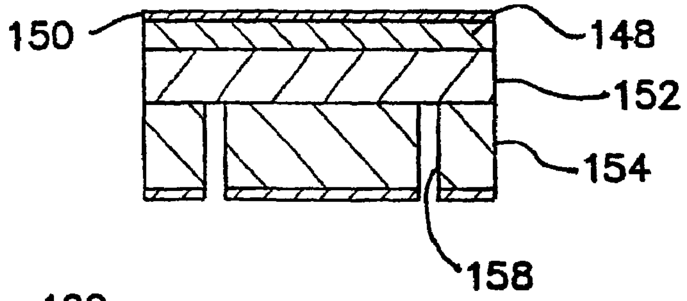
Figure 13C:
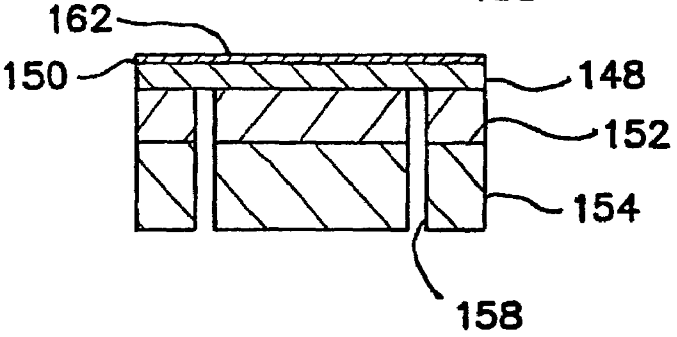

The next step involves the fabrication of membranes by etching through the back of the wafer 154 as shown in the side cross-sectional view of FIG. 13*b*. This may be performed using a Bosch deep reactive ion etch (DRIE) to form trenches 158 through layer 154. For this step the use of a photoresist or oxide mask 156 of approximately six microns is sufficient as shown in FIG. 13*b*. Membranes of 50 $\mu m^2$ have been used, but this is arbitrary and the dimensions to be used are determined by the application. The oxide layer 152 directly under the silicon membrane 148 is then removed from the bottom of trenches 158 with hydrofluoric acid as shown in FIG. 13*c* to define an area which will become membrane 162.

Figure 13D:
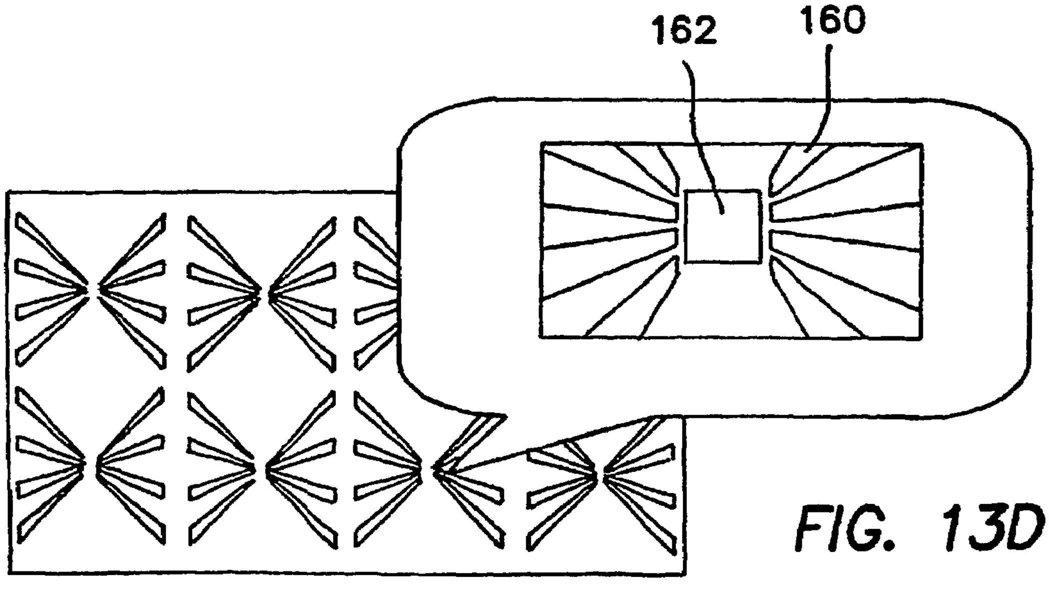

Photolithography and metal deposition is next performed on the top side of the device 10 on layer 150, aligned to the membranes 162, to form the contact pads 160 as depicted in the top plan view of FIG. 13*d* which shows a plurality of dies being simultaneously formed. 30 nm of chrome (as an adhesion layer) followed by 250 nm of Au are deposited in the desired pattern for the bond pads 160 to form ohmic contacts to the boron doped silicon layer 150.

Figure 13E:
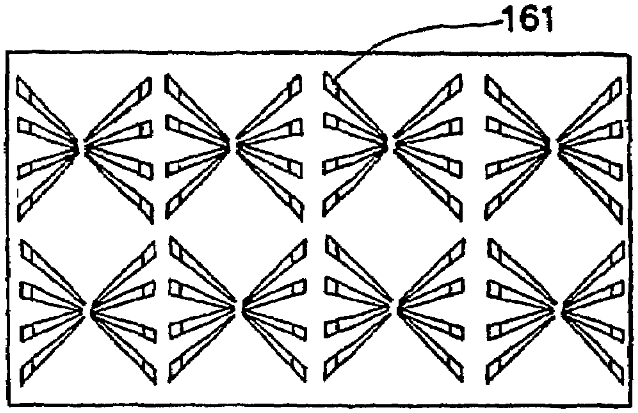
Figure 13F:
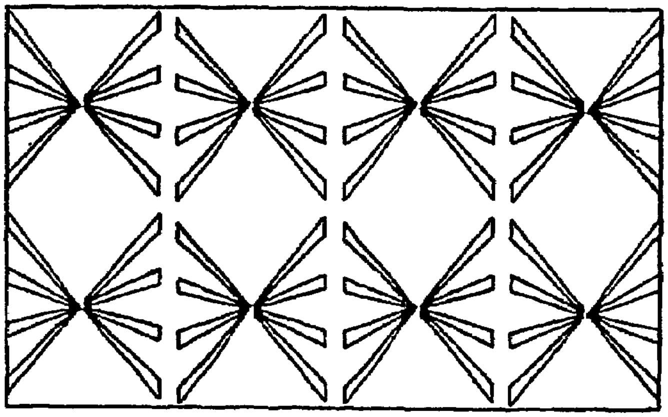
Figure 13G:
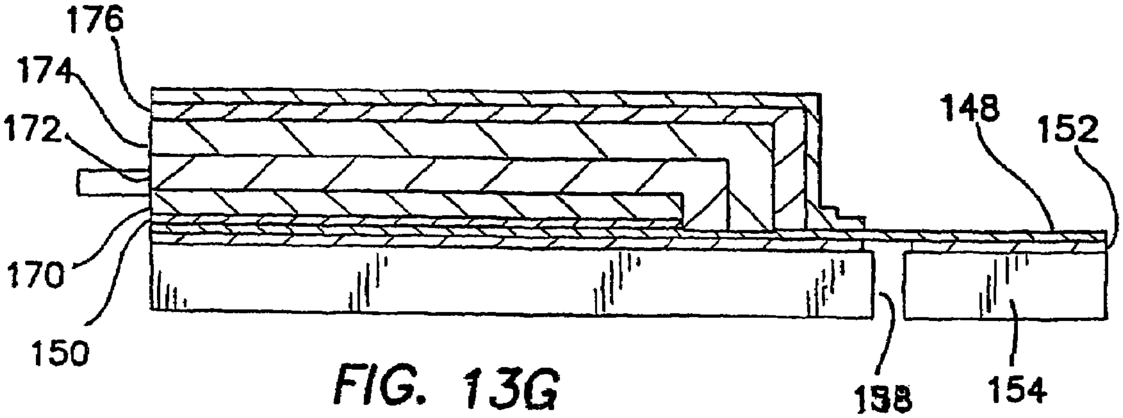
Figure 13H:
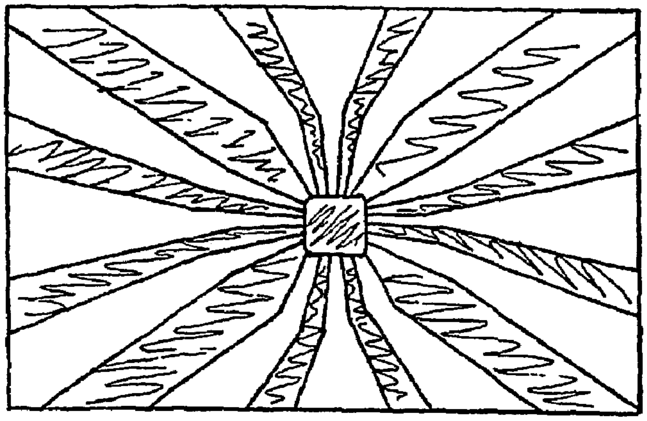

Silicon nitride layer 174 (300 nm) is then deposited over the Au followed by 200 nm silicon dioxide layer 175 to passivate the devices 10 as seen in the top plan view of FIG. 13*e* followed by a layer 176 of chrome as seen in the top plan view of FIG. 13*f* to protect the silicon dioxide 175 during the fabrication process and provide electrical continuity across the step height formed by the passivating layers as shown in FIG. 13*g*.

Figure 13I:
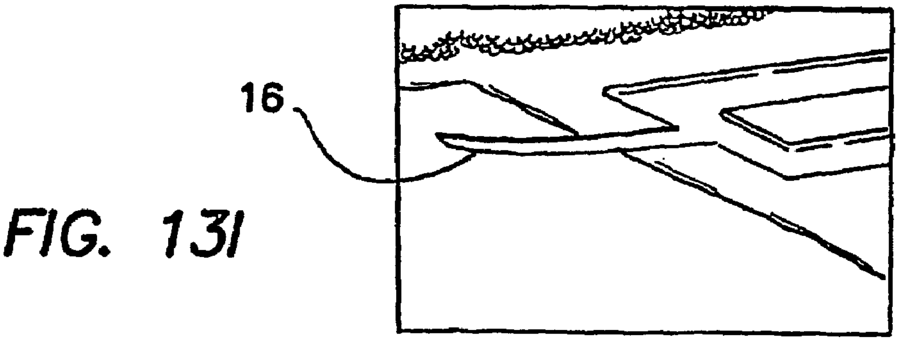

Electron beam lithography is then used to pattern first the gold pads (not shown in drawings) at the tips 14 of where the cantilever 16 will be biofunctionalized and then the cantilevers 16 are patterned (on PMMA) followed by the evaporation of a 30 nm layer 178 (not shown in drawings) of chromium and liftoff as shown in the perspective view of FIG. 13*i*. This portion of the fabrication process involves two steps. First there is the step of disposing a gold square 180 (not shown in drawings) at what will be the tip 14 of the cantilever 16, which will be used for biofunctionalization along with alignment marks (not shown in drawings). The second step is a lithography step which is performed to mask the region which will comprise the cantilever 16 with chrome layer 178 (not shown in drawings).

Figure 13J:
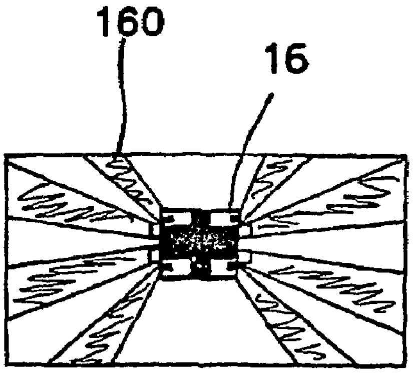

The device 10 is suspended by means of a vertical plasma etch ($NF_3$, $Cl_2$, Ar) which removes the unmasked portions of the membrane defined in layers 150 and 148 resulting in a cantilever 16 as depicted in FIG. 13*i* and in top plan view as shown in FIG. 13*j*. A wet etch is then used to remove the chromium mask 178 (not shown in drawings) and the sample is dried with a critical point dryer. The wafer is diced as shown in the top plan view of FIG. 13*k*.

The microfluidic channels 52 are then fabricated from a silicone elastomer using a patterned photoresist as a mold, which photoresist is then etched away to define the actual flow channels defined in a molded elastomeric encapsulating body 182 as shown in FIG. 131. The flow channels 52 are self-sealing with the silicon of device 10 when placed in an 85° C. oven for 24 hours. The device 10 or gold pad 180 is then biofunctionalized by conventional means as shown in FIG. 13*m*, such as by flowing a fluid through flow channels 52 which fluid carries receptor molecules which preferentially attach to gold pad 180.

Damping Due to Fluff Ball

A fluffball 60, which is nothing more than a large dissipative molecule, is provided with linking receptor molecules 62. The fluffball 60 and linking molecule 62 are free floating in the liquid. Linking molecule 62 is adapted to link to a ligand of interest. Tip 14 is also biofunctionalized with receptors adapted to link to the ligand. Capture of the receptors on tip 14 of the ligand of interest with the receptor 62 and fluffball 60 attached will cause the damping coefficient of tip 14 to dramatically increase.

Figure 14:
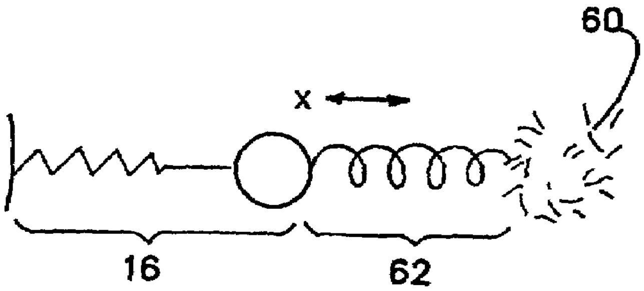
FIG. 14 is a diagram modeling the dynamic action of a cantilever with a molecularly bound fluffball as an added damper.

FIG. 14 is a mathematical model of a cantilever 16 of mass M having a fluff ball 60 attached to its tip 14 by a molecule 62 treated as a spring. The fluffball 60 is devised to maximize dissipation and hence noise and is comprised of a star dendrimer. Molecule 62 may be comprised of an alkane or a ligand chain. The equation for the system of FIG. 14 is:

$$M\ddot{x} + \gamma\dot{x} + \kappa x = k_m(x_d - x) + F$$

$$\gamma_d\dot{x}_d = -k_m(x_d - x)$$

$$x_d = \frac{k_m x}{i\omega\gamma_d + k_m}$$

where M is the mass of cantilever 16, y is the fluidic damping coefficient for cantilever 16, K the spring constant of the cantilever 16, x the displacement of the cantilever tip 14, $k_m$ the effective spring constant of molecule 62 and $x_d$ the displacement of fluffball 60, $y_d$ is the fluidic damping coefficient for fluffball 60, and F is the external force applied to cantilever 16.

The equation of motion for this system can be rewritten to show that there is an effective damping and effective spring constant of the system given by:

$$\overline{\gamma} = \gamma + \frac{\gamma_d}{1 + \left(\frac{\gamma_d}{k_m}\omega\right)^2}$$

$$\overline{\kappa} = \kappa + k_m\frac{\left(\frac{\gamma_d\omega}{k_m}\right)^2}{1 + \left(\frac{\gamma_d\omega}{k_m}\right)^2}$$

The fluffball 60 is chosen so that its damping coeffiecient is as large as possible in order to maximize dissipation and hence the noise so that $$\gamma_d = k_m/\omega$$

$$\overline{\gamma} = \gamma + \frac{1}{2}\frac{k_m}{\omega}$$

The fractional dissipative effect of the biomolecule and fluffball on dissipation and noise is of the order of:

$$\frac{\Delta\gamma}{\gamma} \approx \frac{k_m}{\gamma\omega}$$

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. A submicron bioNEMS device comprising:

a support; and a piezoresistive cantilever coupled to the support extending therefrom with a length I and having a width w and a tip, wherein the cantilever has a restriction portion of reduced width, b, and a length $I_1$, and a biofunctionalized portion at or near the tip.

2. The bioNEMS device of claim 1 where the restriction portion is comprised of multiple legs of reduced width, b, attached to the support.

3. The bioNEMS device of claim 2 where the multiple legs are two in number and are separated from each other by a distance of w−2b.

4. The bioNEMS device of claim 1 further comprising a source of bias current applied to the restriction portion of the cantilever and where the magnitude of the bias current is limited by a maximal acceptable temperature increase at the biofunctionalized tip.

5. The bioNEMS device of claim 4 where the maximal acceptable temperature increase at the biofunctionalized tip is approximately 1 degree K.

6. An improvement in a piezoresistive bioNEMS device immersed in a fluid comprising at least one oscillating cantilever having a length I having a magnitude chosen to minimize background Johnson noise relative to signal strength generated by the piezoresistive bioNEMS device.

7. The improvement of claim 6 wherein the signal strength is based on thermomechanical noise levels of the piezoresistive bioNEMS device in the fluid.

8. The improvement of claim 6 where the piezoresistive cantilever has a width w, and a restriction portion of reduced width, b, wherein the reduced width, b, is chosen to reduce Johnson noise relative to the signal strength generated by the piezoresistive bioNEMS device.

9. The improvement of claim 8 wherein the signal strength is based on thermomechanical noise levels of the piezoresistive bioNEMS device in the fluid.

10. An improvement in a biofunctionalized bioNEMS device immersed in a fluid comprising a receptor disposed on the bioNEMS device for binding to a ligand of interest and a catalyst disposed on the bioNEMS device with the receptor to enhance binding rate coefficients of the receptor with the ligand of interest.

11. The improvement of claim 10 where the catalyst lowers the receptor-ligand binding activation energy.

12. The improvement of claim 10 wherein the receptor is designed by forced evolution to preferentially bind with the ligand of interest.

13. A submicron device comprising:

a source of a carrier signal;

a support;

a piezoresistive cantilever coupled to the support and extending therefrom; and an element disposed on the cantilever and electromagnetically coupled to the source so that the cantilever is driven by the carrier signal from the source.

14. The device of claim 13 where the element comprises a magnetic film disposed on the cantilever, and where the source generates an electromagnetic signal coupled to the magnetic film.

15. An apparatus comprising:

a plurality of NEMS transducers, each of the NEMS transducers generating an output signal; and means for processing the plurality of corresponding output signals from the plurality of NEMS transducers to obtain a collective output signal.

16. The apparatus of claim 15 where the means averages the plurality of output signals so that the collective output signal is an average.

17. The apparatus of claim 15 where the means determines if a predetermined fraction of the plurality of output signals are above a threshold within a predetermined time window.

18. The apparatus of claim 15 where each of the plurality of NEMS transducers are biofunctionalized and where the means effectively increases ligand capture rates by only generating a collective output signal indicative of an increase ligand capture rate as compared to a single one of the NEMS transducers.

19. An apparatus immersed in a fluid comprising a plurality of NEMS transducers immersed in the fluid forming an array of adjacent transducers, each of the NEMS transducers generating an output signal, the motion of two adjacent NEMS transducers being coupled to each through the fluid in which the adjacent NEMS transducers are immersed.

20. The apparatus of claim 19 where a cross correlation of movement of a first and second NEMS transducer comprising the two adjacent NEMS transducers, $C_{12}=<x_1(0)\,x_2(t)>$, is defined by $$\frac{d}{dt}C_{12}(t) = -k_B T X_{12}(t) \text{ for } t > 0$$

where $k_B$ is the Boltzman constant, T is the temperature of the fluid, t is time, and $X_{12}$ the "susceptibility" giving the displacement $x_2(t)$ of the second transducer for a force $F_1$ acting on the first transducer, such that an ensemble average for the position of the second transducer is defined by $$\langle x_2(t)\rangle = \int_{-\infty}^{\infty} X_{12}(t-t')F_1(t')dt'.$$

21. An apparatus immersed in a fluid comprising:
- a microfluidic flow channel for carrying a flow of the fluid; and
- at least one NEMS transducer disposed in the microfluidic flow channel so that a characteristic of the fluid is sensed by the NEMS transducer.

22. The apparatus of claim 21 where the NEMS transducer is biofunctionalized and the characteristic of the fluid is sensed by the NEMS transducer is the presence or absence within the fluid of a ligand to which the NEMS transducer has been biofunctionalized.

23. The apparatus of claim 21 further comprising a plurality of the NEMS transducers, each of which is disposed in common in the flow channel.

24. The apparatus of claim 23 further comprising a plurality of flow channels among which the plurality of NEMS transducers re distributed.

25. The apparatus of claim 23 where the plurality of NEMS transducers are surface fabricated.

26. The apparatus of claim 23 where the plurality of NEMS transducers are membrane fabricated.

27. A method of fabricating a bioNEMS device from a membrane comprising:
- providing a heterostructure comprising a wafer layer, an etch stop layer on the wafer layer, a NEMS device layer on the etch stop layer, and a piezoresistive layer on the NEMS device layer;
- etching trenches through the wafer layer to the etch stop layer to define an area which will become a membrane in which the NEMS device will be defined;
- removing the etch stop layer in the bottom of the trenches to the device layer to form the membrane;
- selectively forming conductive contacts on the piezoresistive layer of the membrane by electron beam lithography;
- selectively forming regions which will become biofunctionalized on the piezoresistive layer of the membrane by electron beam lithography;
- selectively forming a NEMS device on the piezoresistive layer of the membrane by electron beam lithography which include the region which will become biofunctionalized;
- selectively plasma etching the membrane to remove unmasked portions to define a suspended NEMS device;
- selectively molding a flow channel in an elastomeric layer disposed around the membrane; and
- biofunctionalizing selected regions on the NEMS device.

28. The method of claim 27 where providing a heterostructure further comprises polishing the wafer layer to promote adhesion to the elastomeric layer.

29. The method of claim 27 where providing a heterostructure further comprises thinning the wafer layer.

30. The method of claim 27 where selectively plasma etching the membrane to remove unmasked portions to define a suspended NEMS device comprises selectively vertically plasma etching away unmasked portions of the NEMS device layer.

31. The method of claim 27 where selectively molding a flow channel in an elastomeric layer disposed around the membrane comprises selectively disposing a photoresist layer to define the flow channel, disposing an elastomeric layer on the selectively disposed photoresist layer, and removing the photoresist layer to define the flow channel.

32. An NEMS device immersed in a fluid for detecting a ligand comprising:
- a resonating member having a tip immersed in the fluid biofunctiontalized for the ligand;
- a linking molecule disposed in the fluid; and
- a fluffball for providing a damping force disposed in the fluid, wherein capture of the ligand by the linking molecule, and capture of the fluffball by the linking molecule causes increased damping of the member when the ligand is attached to the biofunctionalized tip of the member.

33. The NEMS device of claim 32 where the fluffball is comprised of star dendrimer.

34. A method of detecting a ligand in a fluid by means of a NEMS device comprising:
- immersing the tip of a resonating member in the fluid which tip is biofunctiontalized for the ligand;
- providing a linking molecule disposed in the fluid;
- providing a fluffball in the fluid;
- capturing the ligand by the linking molecule;
- capturing the fluffball by the linking molecule; and
- linking the ligand to the biofunctionalized tip of the resonating member so that damping of the resonating member is increased.

* * * * *